United States Patent
Greene

(10) Patent No.: US 6,454,724 B1
(45) Date of Patent: Sep. 24, 2002

(54) SLEEP APNEA DETECTION SYSTEM AND METHOD

(75) Inventor: Leonard M. Greene, White Plains, NY (US)

(73) Assignee: Safe Flight Instrument Corporation, White Plains, NY (US)

(*) Notice: Subject to any disclaimer, the term of this patent is extended or adjusted under 35 U.S.C. 154(b) by 49 days.

(21) Appl. No.: 09/695,313

(22) Filed: Oct. 25, 2000

(51) Int. Cl.⁷ ................................................ A61B 5/00
(52) U.S. Cl. ........................................................ 600/534
(58) Field of Search ................................. 600/533, 534, 600/538, 586

(56) References Cited

U.S. PATENT DOCUMENTS

| | | | | |
|---|---|---|---|---|
| 4,848,360 A | * | 7/1989 | Palsgard et al. | 600/586 |
| 5,199,424 A | | 4/1993 | Sullivan et al. | |
| 5,540,733 A | * | 7/1996 | Testerman et al. | 600/534 |
| 5,727,562 A | | 3/1998 | Beck | |
| 5,825,293 A | * | 10/1998 | Ahmed et al. | 600/534 |
| 5,989,193 A | * | 11/1999 | Sullivan | 600/586 |
| 6,062,216 A | | 5/2000 | Corn | |
| 6,290,654 B1 | * | 9/2001 | Karakasoglu | 600/538 |
| 6,342,039 B1 | * | 1/2002 | Lynn et al. | 600/538 |

* cited by examiner

Primary Examiner—Robert L. Nasser
(74) Attorney, Agent, or Firm—Dennison, Schultz & Dougherty

(57) ABSTRACT

An apnea monitor and alarm for monitoring the breathing of an individual and for sounding an alarm in response to an interruption in the cyclical rhythm of breathing is disclosed. The monitor and alarm includes a respiration detector, an alarm and a signal processor and analyzer. The signal processor and analyzer is programmed to arm the alarm after a preselected time of cyclical breathing. The signal processor and analyzer is also programmed to sense an interruption in the breathing cycle and to actuate the alarm after a preselected period of interrupted breathing. The monitor and alarm may also include a deactivation system that recycles the program back to an initial part of the program so that the alarm is once again armed after a preselected time of continuous breathing.

6 Claims, 3 Drawing Sheets

SLEEP APNEA DETECTION SYSTEM AND METHOD

FIELD OF THE INVENTION

The invention relates to a sleep apnea detection system and method for detecting apnea and respiratory arrest and more particularly to systems wherein a detector is used in conjunction with an alarm to wake an individual or to summon help to restore a normal an breathing cycle.

BACKGROUND FOR THE INVENTION

Breathing is normally characterized by a regular rhythm of inhaling and exhaling. However, in many individuals apnea or cessation of respiratory airflow causes an interruption in the breathing cycle which can be hazardous to an individual's health. At times such interruption may result in a complete arrest of breathing.

Apnea may be caused by a number of different mechanisms including obstructive episodes in upper airway, by neurologic or disease-medicated lack of diaphragmatic motion, and by a combination of these factors. Some individuals are particularly vulnerable to apnea after general anesthesia. Others receiving epidural narcotics and local anesthetics are at an increased risk of apnea and respiratory arrest.

A number of monitoring devices, have been proposed. For example, some respiration monitors detect the carbon dioxide level in the air which is exhaled by a patient. Other monitors include oxygen monitors as well as instruments which sense motion of the abdomen. Those instruments which detect the motion of the abdomen generally include elastic strain sensing belts, or infrared motion detectors. Other monitors include acoustic detectors to detect the sound of breathing with specially programmed microphones to determine when cessation of breath or lapses in the breathing rate occur, and thus trigger an alarm.

One approach to a sleep apnea detection system is disclosed in the corn U.S. Pat. No. 6,062,216. As disclosed therein, an apnea monitor includes a detector in a fixed console that directs a beam at a sleep surface. The deflection beam is reflected off a patient and the return light is analyzed to develop a signal which varies with external motion of the patient's upper body. The motion signals are then fed to a pattern recognizer which identifies breath signals and analyzes them to detect cessation or excessive pauses in breathing and triggers an alarm or intervention to restore breathing regularity.

It is presently believed that there is a need for an improved sleep apnea detection system in accordance with the present invention. Such systems may be used with various detection systems, i.e. respiration monitors, oxygen monitors, acoustic detectors and the like. The system in accordance with the present invention also includes an automatic trigger device, a delay mechanism for avoiding false alarms, a lock-out feature and an automatic reset feature. The systems are also reliable, relatively inexpensive and durable. In addition, such systems are free of sleep inhibiting or disturbing factors and do not require direct contact with a patient.

The apnea monitor and alarm system or device in accordance with the present invention also minimizes the likelihood of a false alarm and allows an individual to interrupt the cycle in order to leave the room and then to automatically reset the program for continued protection.

BRIEF SUMMARY OF THE INVENTION

In essence, the present invention contemplates an apnea monitor and alarm device for monitoring the breathing of an individual and for sounding an alarm in response to an interruption in the individual's breathing rhythm. The device includes a sensor such as a respiration detector for sensing the cyclical rhythm of the individual's breathing. The device also includes an alarm and first timing means for establishing a first predetermined period of time during which the cyclical rhythm continues and means for arming the alarm in response to the passage of the first predetermined period of time during which the cyclical rhythm continued. In addition, the device includes means inclusive of the sensor means for detecting an irregularity in the cyclical rhythm of the individual's breathing. The apnea monitor and alarm device also includes means for establishing a second predetermined period of time during which an interruption in the cyclical rhythm of breathing continues and means for activating the alarm in response to the passage of the predetermined time during which the interruption in the cyclical rhythm of the individual's breathing continued.

In a preferred embodiment of the invention, an apnea monitor and alarm device includes means for deactivating the alarm and means for automatically reactivating the alarm in response to the passage of the predetermined time during which the cyclical rhythm of breathing continues.

The invention will now be described in connection with accompanying drawings wherein like reference numerals have been used to designate like part.

DESCRIPTION OF THE PREFERRED EMBODIMENTS OF THE INVENTION

Figure 1:
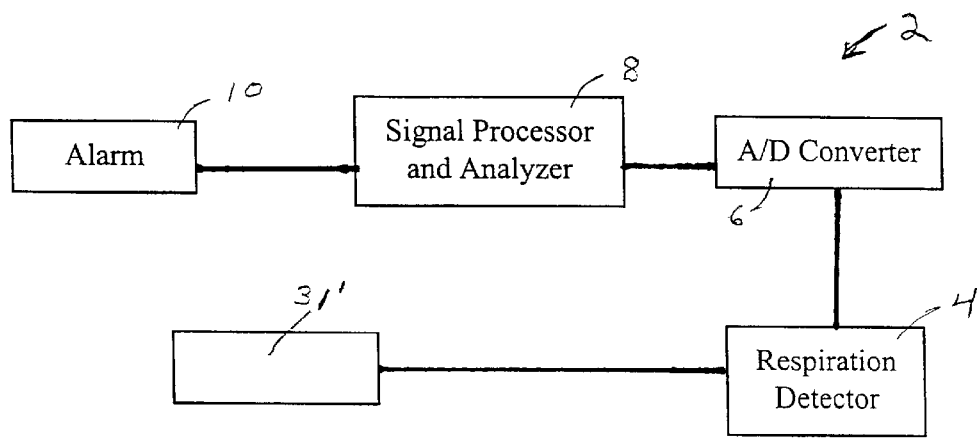
FIG. 1 is a schematic illustration of an individual and an apnea monitor and alarm in accordance with the present invention.
Figure 1:
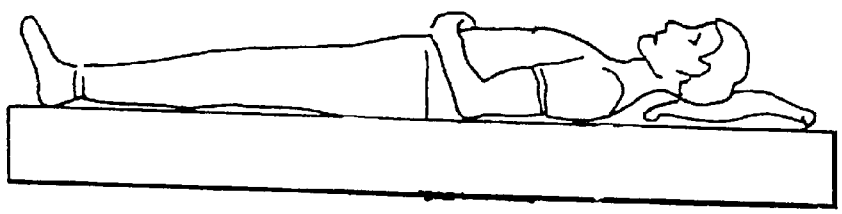

As illustrated in FIG. 1, an apnea monitor and alarm device or system 2 includes a respiration detector 4 which is of conventional design. The detector 4 may, for example, include a pressure transducer or microphone (not shown) which provides respiration signals to an analog to digital converter 6. It is also contemplated that the respiration signal may be provided by a sound transducer and sound communication with the respiratory system of an individual to detect and produce a signal responsive to the sound of an individual's breathing.

The use of a microphone is preferred since it avoids the use of a direct contact with the body by any sleep inhibiting apparatus. However, other forms of detection such as a beam of light reflected by a patient's body as disclosed in U.S. Pat. No. 6,062,216 which is incorporated herein in its entirety by reference may be used. A sensing belt as disclosed in the Beck U.S. Pat. No. 5,727,562 which is also incorporated herein in its entirety by reference may also be preferred particularly when using the apparatus for infants.

The analog to digital converter 6 produces a signal for processing by a signal processor and analyzer 8 which is preferably in the form of a computer or microprocessor. This computer or microprocessor is programmed to perform the functions which will be described hereinafter in connection with FIGS. 2 and 3. As illustrated in FIG. 1, the signal processor 8 is operatively connected to an alarm 10 which may take many forms such as a loudspeaker or the like. Other forms for jarring an individual into an awake state may also be used as will be well understood by persons of ordinary skill in the art.

Figure 2:
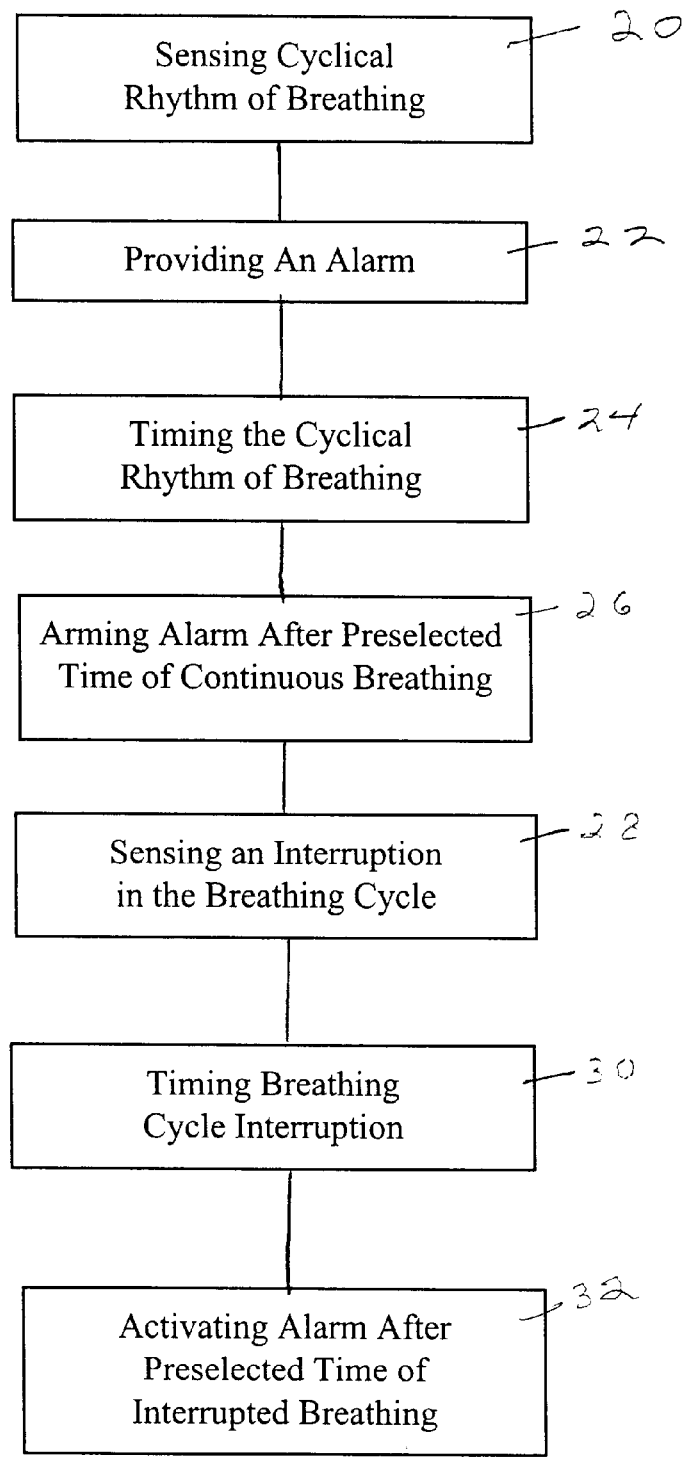
FIG. 2 is a functional block diagram which illustrates the operation of an apnea monitor and alarm system in accordance with a first embodiment of the invention.
Figure 3:
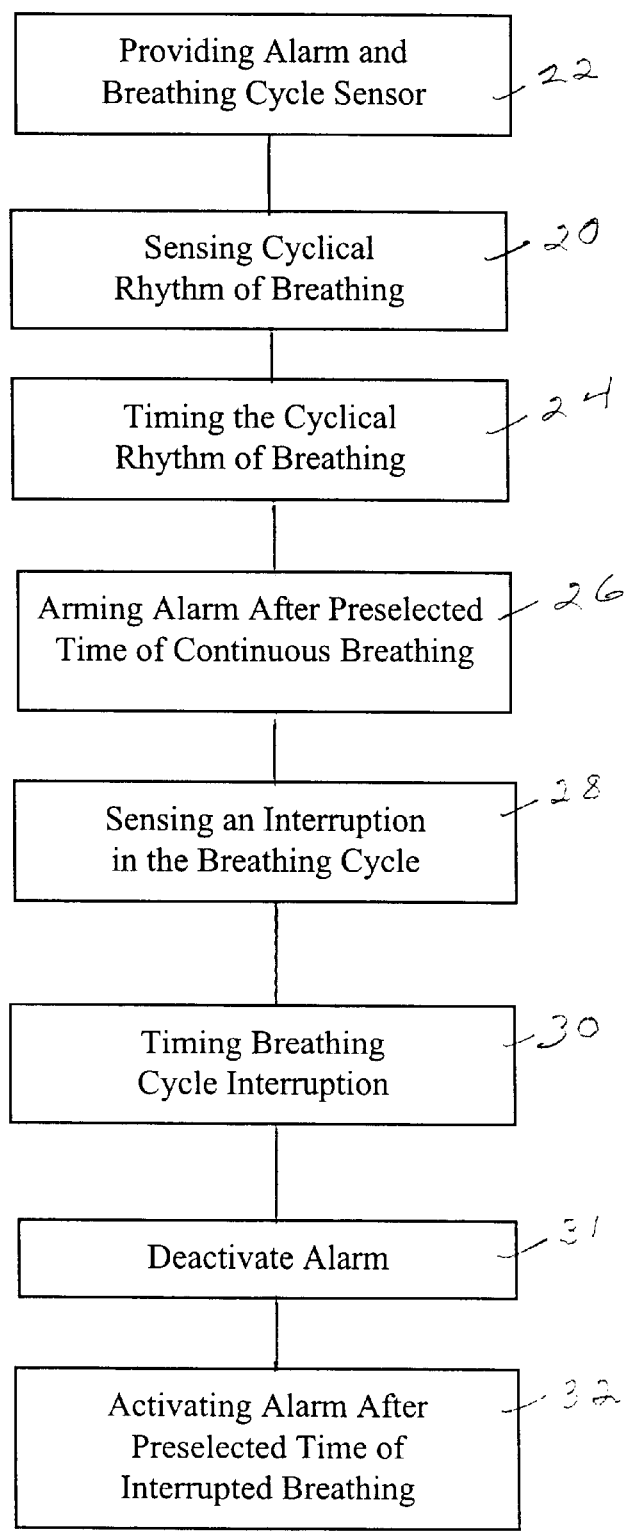
FIG. 3 is functional block diagram which illustrates the operation of an apnea monitor and alarm system in accordance with a preferred embodiment of the invention.

A method and system for detecting apnea and respiratory arrest and alarm to wake the individual or to summon help to restore a normal breathing cycle is illustrated in FIGS. 2 and 3. As shown in FIG. 2, a method includes the step 20 of sensing the cyclical rhythm of an individual's breathing as for example by means of the respiration detector 4 (shown in FIG. 1), A/D converter 6 and signal processor 8 which are shown in FIG. 1. The method also includes the step 22 of providing an alarm and step 24 of timing the cyclical rhythm of breathing.

It is known that an individual's maximum propensity to suffer sleep apnea occurs during REM sleep. Typically, an airway that was otherwise stable may become unstable during REM sleep. It is also recognized that there is usually a period of time which passes between going to bed and falling asleep. Accordingly, an important feature of the present invention resides in a time delay circuit or program which takes effect before arming the alarm. For example, a method in accordance with the present invention includes the step 24 of timing the cyclical rhythm of breathing.

The system 2 also includes a computer program which incorporates a first preselected or predetermined time of about twenty minutes. Then, when the system detects an individual's cyclical rhythm of breathing for that period of time, it arms the alarm 10 as indicated in step 26 of the method.

The method of monitoring the breathing of a subject and for sounding an alarm in response to an interruption in breathing also includes the step 28 of sensing an interruption in the breathing cycle and the step 30 of timing the interruption in the cyclical rhythm of breathing. For example, a computer program for the system 2 also incorporates a second preselected or predetermined time which has a duration of about 2 minutes. This delay is an important feature of the present invention since it eliminates false alarms which would needlessly wake the patient or summon help. However, if the interruption of the breathing cycle continues for the preselected period of time, the alarm is activated as in step 32 of the method. The alarm may be aural such as a loudspeaker, a bright light or other form of alarm which will jar the individual into an awakened state.

In a preferred embodiment of the invention, the system 2 also includes means 12 (FIG. 1) such as a deactivation button for deactivating the alarm. The deactivation of the system as illustrated in connection with the method step 31 (shown as deactivator 31' in FIG. 1) automatically cycles the program back to the sensing of the cyclical rhythm of breathing as indicated in step 20. This feature allows an individual who may get up after a period of sleep, i.e., during the night or other time to leave the room without the alarm sounding and to return to bed without any need to reset the monitor and alarm. This automatic recycling is accomplished using a computer program. Such programs are clearly within the skill of a person of ordinary skill in the art with reference to FIGS. 2 and 3.

While the invention has been defined in accordance with its preferred embodiments, it should be recognized that changes and modifications may be made therein without departing from the scope of the appended claims.

What is claimed is:

1. An apnea monitor and alarm device for monitoring the breathing of a subject and for sounding an alarm in response to an interruption in breathing, said device comprising sensor means for sensing the cyclical rhythm of a subject's breathing, an alarm and first timing means for establishing a predetermined period of time during which said cyclical rhythm continues and means for arming said alarm in response to the passage of the predetermined time during which the cyclical rhythm continued, means including said sensing means for detecting an irregularity in the cyclical rhythm of the subject's breathing and second timing means for establishing a predetermined period of time during which the interruption in the cyclical rhythm of the subject's breathing continues and means for activating said alarm in response to the passing of the predetermined time during which the interruption in the cyclical rhythm of the subject's breathing continued and including means for deactivating the alarm and means for automatically reactivating the alarm in response to the passage of the predetermined time during which the cyclical rhythm has continued.

2. An apnea monitor and alarm device according to claim 1, in which said sensor means is responsive to sound.

3. An apnea monitor and alarm device according to claim 2 in which said sensor means is a sound transducer.

4. A device for activating an alarm in response to an interruption in a breathing cycle of a subject, said device comprising a respiration detector for sensing the cyclical rhythm of a subject's breathing and for generating a signal in response to the cyclical breathing, a signal processor and analyzer, and an analog to digital converter operatively connected to said respiration detector and to said signal processor and analyzer for converting an analog signal to a digital signal, and an alarm, said signal processor and analyzer monitoring the cyclical breathing of a subject and including means for entering a first preselected period of time and for activating said alarm in response to the passage of the preselected period of time during which the sensed cyclical breathing has continued, said signal processor and analyzer including means for entering a second preselected period of time and for detecting an irregularity in the breathing cycle of the subject and initiating an alarm when the period of time of a breathing irregularity exceeds the second preselected period of time to thereby awake the subject, means for deactivating the alarm and means for automatically reactivating the alarm in response to the passage of the first predetermined period of time of a subject's breathing cycle.

5. A device for actuating an alarm in response to an interruption in a breathing cycle of a subject in accordance with claim 4 which the sensor means is a sound transducer.

6. A method for monitoring the breathing of a subject and for sounding an alarm in response to an interruption in the cyclical rhythm of breathing comprising the steps of:

a) sensing the cyclical rhythm of breathing;

b) providing an alarm;

c) timing the cyclical rhythm of breathing;

d) arming the alarm after a preselected time of continuous breathing;

e) sensing an interruption in the cyclical rhythm of breathing;

f) timing the interruption in the cyclical rhythm of breathing;

g) actuating the alarm after the preselected time of interrupted breathing to thereby awaken the subject; and deactivating the alarm and automatically reactivating the alarm after a preselected time of continuous breathing.

* * * * *